US008795323B2

(12) United States Patent
Leschinsky (10) Patent No.: US 8,795,323 B2
(45) Date of Patent: Aug. 5, 2014

(54) DUAL MODE REMOTE ISCHEMIC PRECONDITIONING DEVICES AND METHODS

(75) Inventor: Boris Leschinsky, Mahwah, NJ (US)

(73) Assignee: Infarct Reduction Technologies Inc., Waldwick, NJ (US)

(*) Notice: Subject to any disclaimer, the term of this patent is extended or adjusted under 35 U.S.C. 154(b) by 174 days.

(21) Appl. No.: 13/351,257

(22) Filed: Jan. 17, 2012

(65) Prior Publication Data

US 2013/0184745 A1 Jul. 18, 2013

(51) Int. Cl.
*A61B 17/00* (2006.01)

(52) U.S. Cl.
USPC .......................................................... 606/202

(58) Field of Classification Search
USPC .................................. 606/202, 203
See application file for complete search history.

(56) References Cited

U.S. PATENT DOCUMENTS

| | | | |
|---|---|---|---|
| 5,687,732 A | 11/1997 | Inagaki | |
| 5,968,073 A * | 10/1999 | Jacobs | 606/202 |
| 6,152,881 A | 11/2000 | Raines | |
| 6,805,672 B2 * | 10/2004 | Martin et al. | 600/504 |
| 7,338,410 B2 | 3/2008 | Dardik | |
| 7,717,855 B2 | 5/2010 | Caldarone et al. | |
| 7,885,710 B2 | 2/2011 | Sih et al. | |
| 2005/0004476 A1 * | 1/2005 | Payvar et al. | 600/481 |
| 2007/0150005 A1 | 6/2007 | Sih et al. | |
| 2007/0160645 A1 | 7/2007 | Vinten-Johansen | |
| 2008/0139949 A1 | 6/2008 | Caldarone et al. | |
| 2009/0137884 A1 | 5/2009 | Naghavi et al. | |
| 2009/0287069 A1 | 11/2009 | Naghavi et al. | |
| 2010/0105993 A1 | 4/2010 | Naghavi et al. | |
| 2010/0160799 A1 | 6/2010 | Caldarone | |
| 2010/0185220 A1 | 7/2010 | Naghavi et al. | |
| 2010/0305607 A1 | 12/2010 | Caldarone et al. | |
| 2010/0324429 A1 | 12/2010 | Leschinsky | |
| 2011/0077701 A1 | 3/2011 | Sih et al. | |
| 2011/0190807 A1 | 8/2011 | Redington et al. | |
| 2011/0208099 A1 | 8/2011 | Naghavi | |
| 2011/0224606 A1 | 9/2011 | Shome | |

(Continued)

FOREIGN PATENT DOCUMENTS

| | | |
|---|---|---|
| GB | 2434536 | 1/2007 |
| WO | WO/02/085199 | 10/2002 |

(Continued)

OTHER PUBLICATIONS

Tarakada Y et al. Applications of vascular occlusion diminish disuse atrophy of knee extensor muscles. Medicine & Science in Sports & Excercise, vol. 32, No. 12, 2000, pp. 2035-2039.

(Continued)

*Primary Examiner* — Corrine M McDermott
*Assistant Examiner* — Alexander Orkin
(74) *Attorney, Agent, or Firm* — Boris Leschinsky (57) ABSTRACT

A dual mode automatic device for delivery of remote ischemic preconditioning treatment includes a cuff and a controller configured to deliver a first regular treatment protocol or a second extended treatment protocol. Switching to an extended treatment protocol may be done by an operator for selected groups of patients such as elderly or patients with diabetes. Automatic determination of the best mode is also disclosed. Optimal delivery of remote ischemic preconditioning treatment in this individualized patient-specific manner provides strong ischemic protection to a greater number of patients.

3 Claims, 5 Drawing Sheets

(56) References Cited

U.S. PATENT DOCUMENTS

| | | |
|---|---|---|
| 2011/0238107 A1 | 9/2011 | Raheman |
| 2011/0240043 A1 | 10/2011 | Redington |
| 2011/0251635 A1 | 10/2011 | Caldarone |
| 2011/0319732 A1 | 12/2011 | Naghavi et al. |

FOREIGN PATENT DOCUMENTS

| | | |
|---|---|---|
| WO | WO/2008/70164 | 6/2008 |
| WO | WO/2008/148045 | 12/2008 |
| WO | WO/2008/148062 | 12/2008 |
| WO | WO/2011/005538 | 1/2011 |
| WO | WO/2011/121402 | 10/2011 |

OTHER PUBLICATIONS

Günaydin B, Cakici I, Soncul H et al. Does remote organ ischaemia trigger cardiac preconditioning during coronary artery surgery? Pharmacological Research 41;4:493-496, 2000.

Loukogeorgakis SP et al. Remote ischemic preconditioning provides early and late protection against endothelial ischemia-reperfusion injury in humans. JACC 46;3:450-456, 2005.

Cheung MMH et al. Randomized controlled trial of the effects of remote ischemic preconditioning on children undergoing cardiac surgery. JACC 47;11:2277-2282, 2006.

Ali ZA et al. Remote ischemic preconditioning reduces myocardial and renal injury after elective abdominal aortic aneurysm repair: a randomized controlled trial. Circulation 116:I98-I105, 2007.

Hoole SP et al. Cardiac remote ischemic preconditioning in coronary stenting (CRISP Stent) study: a prospective, randomized control trial. Circulation 119:820-827, 2009.

Rentoukas I et al. Cardioprotective effect of remote ischemic periconditioning in primary percutaneous coronary intervention; enhancement by opioid action. J Am Coll Cadiol Intv 3:49-55, 2010.

Botker He et al. Remote ischaemic conditioning before hospital admission, as a complement to angioplasty, and effect on myocardial salvage in patients with acute myocardial infarction: a randomized trial. Lancet 375:727-34, 2010.

Thielmann M, Kottenberg E, Boengler K, Raffelsieper C, Neuhaeuser M, Peters J, Jakob H and Heusch G. Remote ischemic preconditioning reduces myocardial injury after coronary artery bypass surgery with crystalloid cardioplegic arrest. Basic Res Cardiol 105(5):657-64, 2010.

Walsh SR, Tang T, Sadat U, Dutka DP, Gaunt ME. Cardioprotection by remote ischaemic preconditioning. Br J Anaesthesia 99;5:611-616, 2007.

Hausenloy DJ, Yellon DM. Remote ischaemic preconditioning: underlying mechanisms and clinical application. Cardiovasc Res 79:377-386, 2008.

Tapuria N, Kumar Y, Habib MM, Amara MA, Seifalian AM, Davidson BR. Remote ischemic preconditioning: a novel protective method from ischemia reperfusion injury—a review. J Surg Res 150;2:304-330, 2008.

Walsh SR, Tang TY, Sadat U, Gaunt ME. Remote ischemic preconditioning in major vascular surgery. J Vasc Surg 49:240-243, 2009.

Kharbanda RK, Nielsen TT, Redington AN. Translation of remote ischemic preconditioning into clinical practice. Lancet 374:1557-1565, 2009.

Rohilla A, Rohilla S, Singh G, Singh R. Myocardial ischemic preconditioning: a novel approach to cardioprotection. J Pharm Res 3;1:132-140, 2010.

Kharbanda RK, Mortensen, White PA et al. Transient limb ischemia induces remote ischemic preconditioning in-vivo. Circulation 106:2881-2883, 2002.

Tur E, Yosipovich G, Bar-On Y. Skin reactive hyperemia in diabetic patients: a study by laser doppler flowmetry. Diabetis Care 14;11:958-962, 1991 (Abstract).

Schulman D, Latchman DS, Yellon DM. Effect of aging on the ability of preconditioning to protect rat hearts from ischemia-reperfusion injury. Am J Physiol Heart Circ Physiol 281: H1630-H1636, 2001.

Fromy B, Abraham P, Bouvet C et al. Early Decrease of Skin Blood Flow in Response to Locally Applied Pressure in Diabetic Subjects. Diabetes 51:1214-1217, 2002.

Stewart J, Kohen A, Brouder D et al. Noninvasive interrogation of microvasculature for signs of endothelial dysfunction in patients with chronic renal failure. Am J Physiol Heart Circ Physiol 287: H2687-H2696, 2004.

Tsang A, Hausenloy DJ, Mocanu MM et al. Preconditioning the Diabetic Heart. The Importance of Akt Phosphorylation. Diabetes 54:2360-2364, 2005.

Ferdinandy P, Schulz R, Baxter GF. Interaction of Cardiovascular Risk Factors with Myocardial Ischemia/Reperfusion Injury, Preconditioning, and Postconditioning. Pharmacol Rev 59:418-458, 2007.

Peart JN, Headrick JP. Clinical cardioprotection and the value of conditioning responses. Am J Physiol Heart Circ Physiol 296: H1705-H1720, 2009.

Somers S, Lacerda L, Opie L, Lecour S. Postconditioning the murine heart. Physiological Research (Pre-press article) 2012.

Moro L, Pedone C, Mondi A et al. Effect of local and remote ischemic preconditioning on endothelial function in young people and healthy or hypertensive elderly people. Atherosclerosis 219:750-752, 2011.

Sharma V, Mocanu MM, Kearney M et al. Endothelial dysfunction and/or impaired vascular insulin signalling may have a role in ischaemic preconditioning (Abstract) Heart 97:e8, 2011.

Yin X, Zheng Y, Zhai X et al. Diabetic Inhibition of Preconditioning- and Postconditioning-Mediated Myocardial Protection against Ischemia/Reperfusion Injury. Experimental Diabetes Research vol. 2012: 1-9, 2012.

Abete P, Ferrara N, Cioppa A, Ferrara P, Bianco S, Calabrese C, Cacciatore F, Longobardi G, and Rengo F. Preconditioning does not prevent postischemic dysfunction in the aging heart. J Am Coll Cardiol 27: 1777-1786, 1996.

Fenton RA, Dickson EW, Meyer TE and Dobson JG Jr. Aging reduces the cardioprotective effect of ischemic preconditioning in the rat heart. J Mol Cell Cardiol 32: 1371-1375, 2000.

Tani M, Suganuma Y, Hasegawa H, Shinmura K, Hayashi Y, Guo X, and Nakamura Y. Changes in ischemic tolerance and effects of ischemic preconditioning in middle-aged rat hearts. Circulation 95: 2559-2566, 1997.

Tatsumi T, Matoba S, Kobara M, Keira N, Kawahara A, Tsuruyama K,Tanaka T, Katamura M, Nakagawa C, Ohta B, Yamahara Y, Asayama J, Nakagawa M: Energy metabolism after ischemic preconditioning in streptozotocin-induced diabetic rat hearts. J Am Coll Cardiol 31:707-715, 1998.

Ravingerova T, Stetka R, Pancza D, Ulicna O, Ziegelhoffer A, Styk J: Susceptibility to ischemia-induced arrhythmias and the effect of preconditioning in the diabetic rat heart. Physiol Res 49:607-616, 2000.

Kersten JR, Toiler WG, Gross ER, Pagel PS, Warltier DC: Diabetes abolishes ischemic preconditioning: role of glucose, insulin, and osmolality. Am J Physiol Heart Circ Physiol 278:H1218-H1224, 2000.

Nieszner E, Posa I, Kocsis E, Pogatsa G, Preda I, Koltai MZ: Influence of diabetic state and that of different sulfonylureas on the size of myocardial infarction with and without ischemic preconditioning in rabbits. Exp Clin Endocrinol Diabetes 110:212-218, 2002.

Tosaki A, Pali T, Droy-Lefaix MT: Effects of *Ginkgo biloba* extract and preconditioning on the diabetic rat myocardium. Diabetologia 39:1255-1262, 1996.

Tosaki A, Engelman DT, Engelman RM, Das DK: The evolution of diabetic response to ischemia/reperfusion and preconditioning in isolated working rat hearts. Cardiovasc Res 31:526-536, 1996.

del Valle HF, Lascano EC, Negroni JA, Crottogini AJ: Absence of ischemic preconditioning protection in diabetic sheep hearts: role of sarcolemmal KATP channel dysfunction. Mol Cell Biochem 249:21-30, 2003.

del Valle HF, Lascano EC, Negroni JA: Ischemic preconditioning protection against stunning in conscious diabetic sheep: role of glucose, insulin, sarcolemmal and mitochondrial KATP channels. Cardiovasc Res 55:642-659, 2002.

\* cited by examiner

DUAL MODE REMOTE ISCHEMIC PRECONDITIONING DEVICES AND METHODS

BACKGROUND OF THE INVENTION

The present invention relates generally to methods and devices used for delivery of remote ischemic preconditioning therapy. More particularly, the invention describes an approach to individualize the extent of the ischemic preconditioning stimulus depending on specific patient characteristics.

Ischemia-reperfusion (IR) injury is a composite result of damage accumulated during reduced perfusion of an organ or tissue, and the additional insult sustained during reperfusion. Such injury occurs in a wide variety of clinically important syndromes, such as ischemic heart disease and stroke, trauma, severe blood loss, etc. which are responsible for a high degree of morbidity and mortality worldwide.

During ischemia, anaerobic metabolism predominates and ATP production decreases. There is insufficient available energy to maintain cell membrane pump activity, anti-oxidant defenses, pH and calcium homeostasis, and mitochondrial integrity. These and other consequences of ischemia inevitably lead to cell death, unless blood flow is restored. Though reperfusion with oxygenated blood is essential for any tissue salvage, the sudden influx of oxygen leads to the formation of reactive oxygen species. A key event in cell death is mitochondrial permeability transition, a phenomenon that occurs when the mitochondrial permeability transition pore becomes permeable to molecules of about 1500 kDa or smaller. This leads to a rapid influx of small molecules, mitochondrial swelling and subsequent cell death.

Strategies to limit the duration of ischemia have achieved substantial health gains in myocardial infarction, and to a lesser degree, stroke. However, door-to-needle times have likely reached the minimum that is possible in many healthcare delivery systems, so further reduction in morbidity and mortality from IR injury will require strategies to increase tissue tolerance to ischemia or reduce damage that occurs on reperfusion.

One such approach is ischemic preconditioning, and its variant—remote ischemic preconditioning. This treatment has been shown to be the most powerful intervention to stimulate innate resistance of tissues to ischemia-reperfusion injury. The term "ischemic preconditioning" is used in this description in a broad sense and includes a range of interventions known in the literature as "ischemic conditioning", "ischemic peri-conditioning", "ischemic per-conditioning", and "ischemic post-conditioning"—in other words, it describes a series of intermittent ischemic episodes applied to a subject at some point before, during, or after the ischemic event and/or restoration of perfusion.

In general terms, the concept of remote ischemic preconditioning (RIPC) describes a series of intermittent occlusions of blood flow to a limb of a subject. Typically, a 5 min interval of occlusion is accomplished by inflating a cuff on a subject's upper arm to a sufficiently high cuff pressure. Deflation of the cuff causes release of occlusion and restoration of blood flow, which is maintained for another 5 min or so. This treatment cycle is repeated two or three times for a total duration of therapy of about 30-40 min.

RIPC activates three main cell-signaling pathways, the cyclic guanosine monophosphate/cGMP-dependent protein kinase (cGMP/PKG) pathway, the reperfusion injury salvage kinase (RISK) pathway, and the survivor activating factor enhancement (SAFE) pathway. Some of these pathways overlap, in particular where they converge on the mitochondria. Here, the potassium dependent ATP ($K_{ATP}$) channel is activated with evidence that this leads to closure of the mitochondrial permeability transition pore. RIPC also initiates a complex genomic and proteomic response that underpins the late phase of protection, including a plethora of anti-apoptotic and anti-inflammatory gene transcriptions.

Triggers in the initial cascade recruit early mediators such as protein kinase C (PKC), tyrosine kinase, phosphatidylinositol 3-kinases (PI3K), protein kinase B (PKB or Akt), mitogen-activated protein kinases (MAP1/2 or MEK1/2), extracellular signal-regulated kinases (Erk1/2), and janus kinase (JAK), which activate transcription factors such as signal transducer and activator of transcription proteins (STAT1/3), nuclear factor kappa-light-chain-enhancer of activated B cells (NFκB), activator protein 1 (AP-1), nuclear factor-like 2 (Nrf2) and hypoxia inducible factor 1α (HIF-1α). Systemic spread of protection involves both humoral and neuronal pathways.

A number of automatic devices and methods for delivery of remote ischemic preconditioning therapy have been described in the prior art. Caldarone (U.S. Pat. No. 7,717,855, US Patent Application Pub. Nos. 2011/0251635, 2010/0305607, 2010/0160799), Redington (PCT publication WO 2011/121402), Raheman (US Patent Application No. 2011/0238107), Naghavi (US Patent Application Pub. Nos. 2009/0287069, 2010/0105993, 2011/0319732), and my US Patent Application Pub. No. 2010/0324429 all describe various devices designed for this purpose. These documents are incorporated herein in their respective entireties by reference.

Activation of complex defensive response triggered by an ischemic preconditioning stimulus may be impaired in some categories of patients such as elderly or diabetics. Prior art devices have a predetermined and usually fixed preconditioning treatment protocol, which may not account for particular needs of such special patient groups. New devices and methods are therefore needed to provide as many patients as possible with the benefits of robust protection against reperfusion injury which are afforded as a result of applying remote ischemic preconditioning therapy.

SUMMARY OF THE INVENTION

Accordingly, it is an object of the present invention to overcome these and other drawbacks of the prior art by providing novel methods and automatic devices to fully trigger innate ischemic tolerance via application of remote ischemic preconditioning therapy in a diverse group of patients including those with a variety of preexisting conditions, which may otherwise reduce the efficacy of this procedure.

It is another object of the present invention to provide novel RIPC devices allowing for selection of the most appropriate patient-specific RIPC treatment protocol depending on a patient's preexisting condition.

It is a further object of the present invention to provide diagnostic methods allowing automatic selection of the most appropriate patient-specific RIPC treatment protocol.

It is yet a further object of the present invention to provide methods and devices allowing such diagnostic determination to occur concurrently with RIPC delivery so as not to extend the overall duration of the therapy.

The present invention provides for at least two modes of operation for an automatic RIPC device. Such device may be configured for initial activation in a first or regular RIPC mode, such as for example to deliver a first treatment protocol of 3 or 4 cycles of 5-min occlusion and 5-min release. If at some point before, during or shortly after the completion of the first ischemic preconditioning treatment protocol the patient is identified as having one or more preexisting conditions, comorbidities, or risk factors known to attenuate RIPC efficacy, a second mode of RIPC delivery may be activated according to a second RIPC treatment protocol designed to increase the overall intensity of an ischemic preconditioning stimulus. Greater ischemic stimulus of the second RIPC treatment protocol in a second mode may be sufficient to overcome a higher response threshold for such patients and fully trigger innate ischemic protection mechanisms, which may be otherwise dormant and not respond to the first RIPC stimulus. Activation of the second RIPC treatment protocol may be accomplished by pushing a button on a controller. A first indicator to confirm activation of the second treatment protocol may be provided for the operator, such as a visual display indicator.

A need to switch to the second mode may be identified by examining patient's preexisting conditions. Advanced age, diabetes (both type I and type II) or other preexisting conditions may prompt a operator to manually activate a second mode in which a longer ischemic preconditioning stimulus is delivered.

Alternatively, assessing tissue perfusion may be used for such identification. Flow-mediated dilatation is a process of regulation of blood flow in which increased tissue perfusion follows an interval of ischemia. The extent by which maximum tissue perfusion exceeds the steady-state tissue perfusion may be used for automatic detection of the need for using a longer ischemic preconditioning stimulus. Methods and device configurations are discussed allowing for automatic determination of a need to switch to the second mode by analyzing a tissue perfusion response during one or more ischemic preconditioning treatment cycles conducted at the beginning of the procedure.

In embodiments, the device of the invention comprises a disposable cuff containing an inflatable portion, the cuff is sized to be placed on a limb of a subject; and a reusable controller removably attached to the cuff with a releasable fastener, the controller is attached to the cuff on the outer side of the inflatable portion of the cuff, the controller is operably connected to the inflatable portion of the cuff via a releasable pneumatic coupling; the controller is configured to cause inflations and deflations of the inflatable portion of the cuff according to an ischemic preconditioning treatment protocol as described herein, whereby when the device is used on either a right limb of the subject or a left limb of the subject the controller is positioned to face an operator and the inflatable portion of the cuff is positioned over the main artery of the respective limb. The controller may be battery-powered and configured to be disconnected from the cuff and recharged between uses.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF THE FIRST PREFERRED EMBODIMENT OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Figure 1:
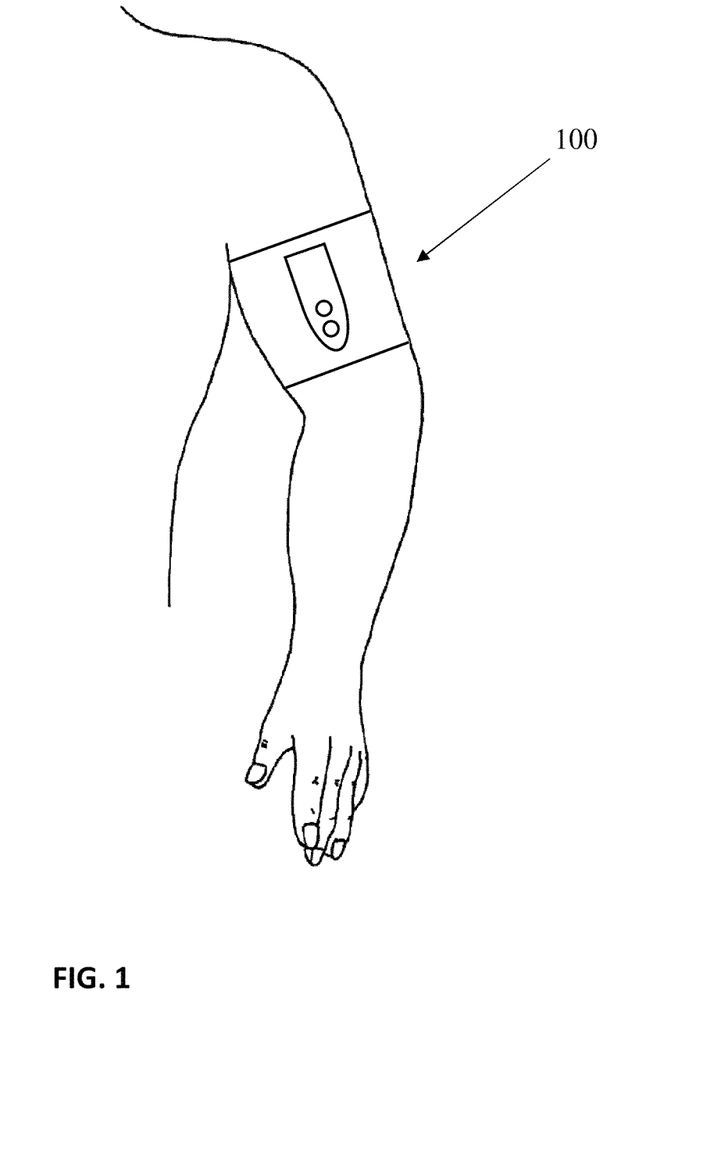
FIG. 1 is general view of an automatic ischemic preconditioning device placed on a limb of a subject.
Figure 2:
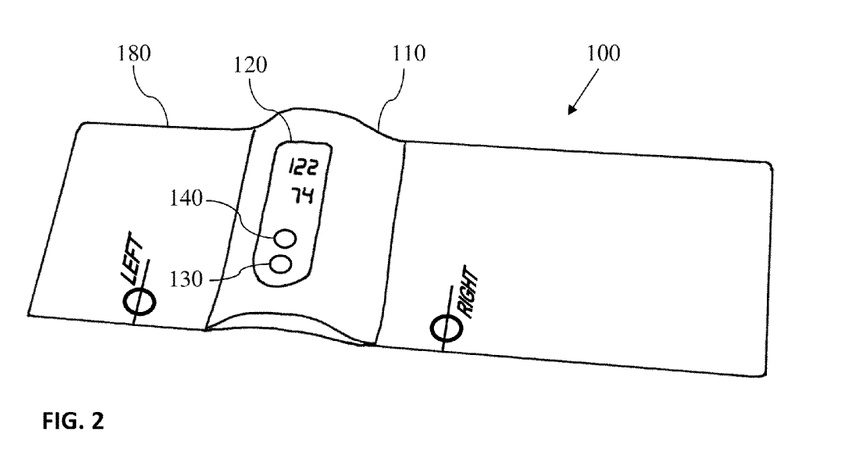
FIG. 2 is a general view of a dual mode automatic remote ischemic preconditioning device of the present invention.

FIG. 1 generally shows a device of the present invention in use on a subject. The device 100 may be placed on an upper arm or a thigh of the subject. It generally includes an inflatable cuff 180 and a controller 110 as shown in FIG. 2. The cuff 180 may include an inflatable bladder or may be configured to be inflated without the bladder. The cuff 180 may be appropriately sized to fit about the limb of a subject. Several fixed sizes of cuffs may be offered depending on the size of the subject—from neonate to large adult as well as an additional "thigh" size. The cuff 180 may also be made adjustable to fit a broad range of patients. In embodiments, the cuff 180 may include a Velcro or other type of fastener allowing for tight fit of a cuff about the limb of a subject in a deflated state with one end overlapping the other end (shown in FIG. 8 as position 285 on the internal surface of the cuff). The cuff 180 may contain indicia instructing the operator how to position the device on the right upper arm of the subject or the left upper arm of the subject so that the inflatable portion of the cuff may be located over the corresponding right or left brachial artery. Such indicia may be a line indicating a proper position over the left brachial artery with the word "LEFT" and another line for guiding the placement of the device over the right brachial artery with the word "RIGHT". The term "operator" is used in this description to describe a person who activates and controls the device, such as a clinician (a doctor or a nurse) or a patient in case of self-administration of the therapy.

Either the cuff 180 or the controller 110 may be configured to be disposable of reusable. In embodiments, the entire device may be disposable in which case the controller 110 may be fully integrated with the cuff 180. The batteries and other electronic parts of the controller may be still made removable for proper recycling after the use of the device is complete. Measures may be deployed to disable the device after its intended use period so as to prevent additional unauthorized uses, which may be unsafe due to battery depletion.

In other embodiments, the device 100 may be configured to include a disposable cuff 180 and a reusable controller 110, which may contain rechargeable batteries. Once recharged, the batteries may be sized to provide sufficient power for one full treatment protocol, in a first or in a second mode. In other embodiments, the batteries are selected to provide sufficient electrical power for two treatment protocols so as to account for a possibility of the subject transfer from one hospital to another or any other delays in revascularization and perfusion restoration therapy.

For a "disposable cuff—reusable controller" configuration, the cuff 180 may have at least one releasable fastener allowing it to detachably retain the controller 110 on the outer side thereof facing the operator. In embodiments, the controller 110 may be positioned over the inflatable portion of the cuff 180 such as for example between the LEFT and RIGHT indicia marks. This assures the controller to face the operator when the device is used on either the left upper arm or the right upper arm of the subject. At the same time, the inflatable portion of the cuff may be located over the respective main artery of the limb such as a brachial artery of the upper arm. The cuff 180 and the controller 110 may further include a releasable pneumatic coupling such that when assembled together using the releasable fastener, the pneumatic portion of the controller 110 is operably connected via a pneumatic seal to the inflatable portion of the cuff 180. The controller 110 may have a curved surface facing the limb of the subject so as to assure a good fit over the subject's limb. The controller 110 may be battery-powered and configured to be detached from the cuff 180 and recharged between uses.

In embodiments, the inflatable portion of the cuff may constitute a large part of or the entire cuff 180. In that case, the cuff 180 may be made to be circular and without a Velcro-type fastener to connect both ends of the cuff together. A subject's limb may be placed inside such circular "doughnut-like" cuff. Inflation of the cuff may cause the entire periphery of the limb to be compressed by pressurized air. One advantage of such arrangement is that the controller 110 may be easily placed on top of the limb facing the operator regardless of whether the right or the left arm of the subject is used for the therapy. Another advantage is that one large diameter cuff will fit many or even all subjects, whereby reducing the need to stock various sizes of the device. At the same time, increased volume of compressed air in a large circular inflatable portion of the cuff may make blood pressure readings more difficult, especially when the subject is being moved, as movement may cause pressure reading artifacts.

The controller 110 may include a display 120 for communicating to the operator the status of device, progression of therapy and other procedure details. The controller may include a START button 130 configured to initiate the treatment. The controller 110 may be configured to conduct the entire procedure automatically after the START button is initially depressed so as not to require further operator intervention. In that case, the controller 110 may be configured to detect subject's blood pressure or utilize another method to inflate the cuff 180 to a sufficiently high cuff pressure so as to occlude blood flow through the limb according to a remote ischemic preconditioning treatment protocol.

The controller 110 may be further configured to delay the initiation of the remote ischemic preconditioning treatment for a pre-specified period of time (such as 10 min, 30 min, 60 min etc.) after pressing the START button. Such delay may be helpful in assuring completion of the procedure just in time for perfusion restoration, when such time can be predicted with reasonable certainty, for example when performing elective cardiac or other surgery.

The device 100 of the invention may be inflated using compressed air. For that purpose, the controller may be operatively connected with or may include an incorporated air pump, one or more valves, one or more pressure sensors or other sensors, a plug-in or portable energy source (such as disposable or rechargeable batteries), as well as an electronic processing unit programmed for operating various elements of the device. A number of designs and configurations of a remote ischemic preconditioning device useful for the purposes of this invention are described in more detail in my above-cited U.S. patent application Ser. No. 12/820,273 entitled "METHODS AND DEVICES FOR REMOTE ISCHEMIC PRECONDITIONING AND NEAR-CONTINUOUS BLOOD PRESSURE MONITORING".

Various other device configurations are also contemplated in this disclosure including incorporating a controller into a larger medical device such as a patient monitor designed for collecting various physiological parameters of the subject, in which case the cuff 180 may be connected to the controller by a flexible tube. Automatic operation of the device may be controlled locally from an appropriate processor or remotely from a processor located at another location via commonly known wireless or wired communication protocols.

To achieve an ischemic preconditioning effect, the controller may be configured to inflate the cuff 180 to a pressure sufficient to largely (by at least 90% or more) or entirely occlude limb blood flow. As described in my above cited patent application, to reach the pressure needed for such occlusion, the cuff needs to be inflated to at least a limb occlusion pressure. Depending on a number of factors including the width of the cuff, the limb occlusion pressure may be below, at or above the subject's systolic blood pressure. The controller may be configured to measure systolic blood pressure of the subject and calculate the limb occlusion pressure at least once or preferably several times during the treatment. The cuff may then be inflated to a fixed or a variable target pressure at or above the limb occlusion pressure during the occlusion interval. Periodic measurements of systolic blood pressure during the treatment may be used to adjust the cuff pressure inflation target following the changes in subject's blood pressure.

As described in more detail above, the mechanism of protection activated by a series of intermittent blood flow occlusions is a complex process involving delicate interactions of various cell signaling mechanisms. Activation of this complex defensive response triggered by an ischemic preconditioning stimulus may be impaired in some categories of patients. Diabetes and advanced age are two examples of special patient groups that may have a reduced response or even no response to a regular ischemic preconditioning stimulus, which is otherwise effective for other patients. These groups constitute a large proportion of patients experiencing a heart attack. In fact, up to 25% of all AMI patients are diabetics. As to elderly, about 40% of all patients diagnosed with the myocardial infarction or fatal coronary heart disease are over the age of 75 (Heart Disease and Strokes Statistics—2011 Update, published by American Heart Association, *Circulation,* 2011). In addition to being a likely group with diminished response to ischemic preconditioning, these patients are at the highest risk of dying from the heart attack, making them especially vulnerable to mortality and morbidity as a consequence of the heart attack.

Other preexisting conditions or comorbidities that may diminish the ability of RIPC to fully trigger robust ischemic protection may include obesity, advanced atherosclerosis, dyslipidemia, hypertension, cardiac hypertrophy, heart failure, history of smoking, history of alcohol or substance abuse, and various pharmacological interactions. Common compounds that may interfere with ischemic preconditioning may include statins, beta-blockers, non-steroidal anti-inflammatory drugs (such as aspirin), $Ca^{2+}$ channel blockers, recent or excessive caffeine intake, hypoglycemic sulfonylureas, and insulin.

For these patients, a longer preconditioning stimulus may be required to reach their elevated threshold and fully trigger their protective response.

In embodiments, the controller 110 may be configured to have a first mode of operation and a second mode of operation. In the first mode, the controller 110 may be configured to cause inflations and deflations of the cuff 180 according to a first treatment protocol, which includes a first predetermined number of treatment cycles, each of said cycles including:
   inflating the cuff to a cuff pressure at or above a limb occlusion pressure of the subject,
   maintaining the cuff pressure at or above the limb occlusion pressure for a first occlusion interval of at least about one minute,
   deflating the cuff to a deflated state, and
   maintaining the cuff in the deflated state for a first release interval.

The controller 110 may be further configured to cause the inflation and deflation of the cuff 180 according to a second treatment protocol, which may be characterized by a second predetermined number of treatment cycles, each cycle including:
   inflating the cuff to the cuff pressure at or above the limb occlusion pressure of the subject,
   maintaining the cuff pressure at or above the limb occlusion pressure for a second occlusion interval of at least about one minute,
   deflating the cuff to the deflated state, and
   maintaining the cuff in the deflated state for a second release interval.

The second treatment protocol may be longer than the first treatment protocol by a number of treatment cycles or total treatment time.

In embodiments, the controller 100 may be configured to activate the second mode or switch to a second mode from a first mode based on an input signal. Such input signal may be generated using a manual input from an operator. For that purpose, the controller 110 may include a button 140 configured when depressed to activate or switch to a second mode of ischemic preconditioning therapy. The term "button" is used in this description in a broad sense to include other suitable controls allowing switching to a second mode. Such controls may include real or virtual (such as when using a touch-sensitive display) buttons, knobs, sliders, dials, selectors etc. configured to allow selection of the number of treatment cycles as well as adjusting of durations of various treatment intervals.

The controller 110 of the device 100 may also include a visual and/or audible first indicator configured to communicate to the operator whether the device is currently executing the first or the second treatment protocol. Such indicator may be made in a form of a light, a symbol on a display, a lighted button used to turn on the second mode, etc. The same or a separate indicator may also be used to show the progression of treatment and remaining time needed to finish the procedure.

In embodiments, the controller 110 may be configured to deliver the entire remote ischemic preconditioning therapy in the first mode using a first treatment protocol. The controller 110 may also be configured to activate the second mode before and in place of the first mode. The controller 110 may further be configured to switch from a first mode to a second mode at any time during or shortly after the completion of the first treatment protocol. The switching from one mode to another may be done based on the above mentioned input signal such as a manual input from the operator. In other embodiments. the controller 110 may also be configured to generate the input signal and select the most appropriate treatment mode automatically by performing tissue perfusion or other tests during the progression of therapy as described in more detail below.

Figure 3:
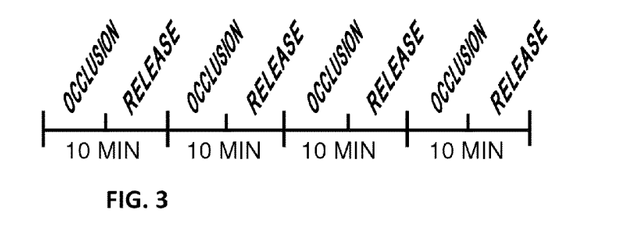
FIG. 3 shows an example of a first treatment protocol for delivery of a first ischemic preconditioning stimulus.

A first ischemic preconditioning treatment protocol may be sufficient for majority of patients without the preexisting conditions described above. The advantage of operating the device in the first mode is that the therapy may be delivered over less time than when using a second mode. The first treatment protocol may be characterized by a first predetermined number of treatment cycles as well as durations of respective occlusion and release intervals. In a typical example of a first treatment protocol, the controller may be programmed to deliver three or four treatment cycles, each cycle consisting of 3-5 min occlusion and 3-5 min release intervals—see FIG. 3. Each treatment cycle may have equal durations of occlusion and release intervals or such durations may be uneven, for example occlusion may be longer than release. Typically, 5-30 min of total occlusion time may be sufficient time for RIPC purposes in the first mode.

Figure 4:
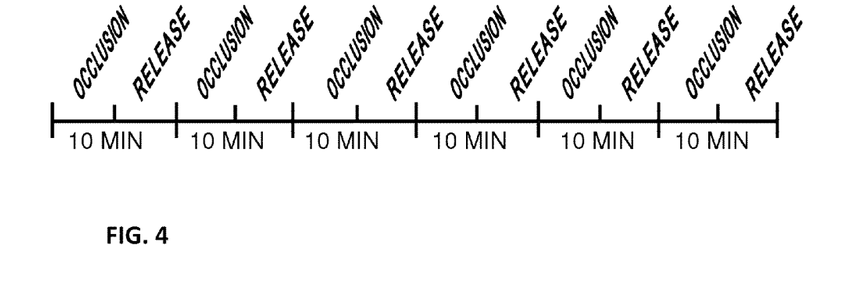
FIG. 4 shows an example of a second treatment protocol with increased number of treatment cycles.

In embodiments, one example of the second ischemic preconditioning treatment protocol is when the total number of treatment cycles exceeds that of the first treatment protocol. Four to eight treatment cycles may be used to achieve a greater intensity of ischemic preconditioning stimulus. FIG. 4 shows an example of the second treatment protocol with six treatment cycles, each cycle being identical to that of the first treatment protocol shown in FIG. 3.

Figure 5:
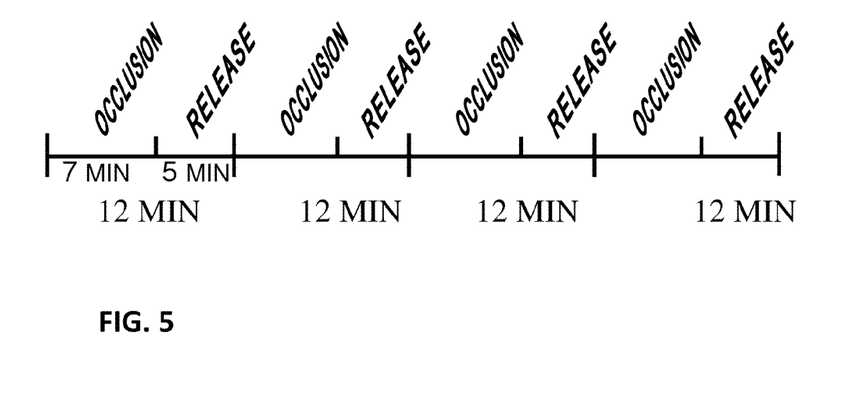
FIG. 5 shows an example of a second treatment protocol with increased duration of occlusion intervals.

Another example of the second treatment protocol is shown in FIG. 5. The duration of each occlusion interval is greater than that of a corresponding first treatment protocol. In this example, each occlusion interval is 7 min long as opposed to 5 min for the first treatment protocol. In embodiments, each occlusion interval may last between 5 and 10 min. Release intervals may be the same as with the first treatment protocol (see FIG. 5). Release intervals may also be shortened or extended. In embodiments, the duration of one or more release intervals may be selected to be between 3 and 10 min.

Executing the second treatment protocol will increase the total treatment time as compared with the treatment time of the first treatment protocol. One advantage of increasing the duration of the occlusion interval rather than increasing the total number of cycles is that the total treatment time may be not as long in that case. In embodiments, the treatment time of a second treatment protocol may be selected to be greater than the treatment time of the first treatment protocol by 1 to 150 percent.

In use, the device 100 may be placed on a subject that may benefit from a remote ischemic preconditioning therapy. This may be a subject suffering from a heart attack or stroke for example. The device may be activated by pushing a START button. A default mode of operation may be to deliver the first treatment protocol upon activation of the device. Unless the second mode is initiated, the procedure will be completed in the first mode of operation.

If at some point before, during or shortly after the completion of the first treatment protocol, the subject is identified as having at least one of above cited preexisting conditions known to attenuate the effects of the ischemic preconditioning therapy, the operator may switch the device to the second mode of operation.

If such subject is identified before starting the procedure, such as in most routine uses of the therapy, for example prior to scheduled surgery, the second treatment protocol may be activated right at the beginning of the treatment.

If the first mode of treatment has already been started, switching to the second mode may depend on the design of the second treatment protocol. If the second treatment protocol consists of a greater number of treatment cycles, the switching process to such treatment protocol is fairly straight forward. The controller 110 may be programmed to keep track of the already executed treatment cycles. Upon activation of the second mode, the controller may be programmed to continue the treatment until the total number of executed treatment cycles matches the desired target number of cycles for the second treatment protocol.

The controller may be activated to deliver additional treatment cycles even shortly after completion of the first treatment protocol. In various embodiments of the invention, the controller may be programmed to accept the input signal from the operator and switch to the second treatment protocol at 10, 20, or 30 min after the completion of the last occlusion interval of the first treatment protocol.

If the second treatment protocol involves longer occlusion intervals and optionally greater number of treatment cycles, the controller may be configured to start the second treatment protocol anew if only a small portion of the first treatment protocol has been completed, such as for example one treatment cycle. If switching occurs later in the procedure, a blended treatment protocol may be implemented. One example of a blended protocol involves achieving a desired total duration of occlusion minutes. For example, if the first treatment protocol calls for 4 cycles of 5 min occlusion and 5 min release cycles and the switching occurs after 2 cycles have been completed (10 occlusion minutes), the controller may be configured to deliver the remaining 20 occlusion minutes in three cycles of 7, 7, and 6 minutes interspersed with 5 min release intervals. That would bring the total number of occlusion minutes to 30, which may be a predetermined target programmed in the controller 110 processing unit. To achieve a proper blended treatment protocol, other desired parameters of the second treatment protocol may be predetermined, such as for example total treatment time, individual maximum durations of one or more occlusion and release intervals, cumulative occlusion duration or cumulative release duration. Depending on when the switching occurs, the controller may be programmed to determine the remaining blended treatment schedule automatically using one or more of these parameters.

Executing the second treatment protocol will prolong the duration of therapy. In embodiments, the treatment time of the second treatment protocol may exceed that of the first treatment protocol by 1 to 150 percent. For emergency cases, such as heart attack or stroke, any delay in definitive perfusion restoration treatment (such as restoration of blood flow via a percutaneous coronary intervention), may be undesirable. To address this concern, it is proposed to allow perfusion restoration therapy to commence when a sufficiently large portion of the ischemic preconditioning treatment has taken place. At the same time, remaining portion of the ischemic preconditioning treatment protocol may still be delivered uninterrupted after the blood flow to the ischemic organ has been restored.

In embodiments, the device 100 may include a second indicator to communicate to the operator when it is advisable or when it is not advisable to start a definitive perfusion restoration therapy. The second indicator may be automatically operated to be turned on to prompt for perfusion restoration at any suitable point of time starting at least at or past the midpoint of the ischemic preconditioning treatment. In other embodiments, that indicator may be operated at a 75% completion point of the ischemic preconditioning treatment. Yet, in other embodiments, it may be activated only when the entire ischemic preconditioning treatment protocol is fully executed. In yet other embodiments, the second indicator may be configured to communicate to the operator that the ischemic preconditioning protocol has not yet reached the point when the perfusion restoration therapy may be safely initiated. In this case, the second indicator may be turned off by the controller to prompt for perfusion restoration therapy to proceed.

Given a temporary nature of the ischemic protection after the completion of the ischemic preconditioning treatment, the second indicator may be configured to communicate the appropriate window of time when perfusion restoration therapy should ideally take place. In that case, the second indicator may be turned on to prompt for perfusion restoration at some time before or at completion of the remote ischemic preconditioning treatment protocol and turned off about 2 hours after the completion of the treatment protocol. Turning the second indicator off or otherwise communicating to the operator that the appropriate window of time for perfusion restoration therapy has closed may be useful to communicate to the operator that another preconditioning treatment may be necessary if perfusion to ischemic organ or tissue has not been yet restored. A count-down timer may also be implemented to continuously communicate the time remaining in perfusion restoration window during which the ischemic protection remains in full effect.

In embodiments, a third or more additional modes may be provided by the controller 110. More than two modes may be provided for patients having not one but several of the preexisting conditions as described above. In this case, the first mode may be activated by default and may provide adequate results for subjects without above listed preexisting conditions. The second mode may be selected to be longer than the first mode and may provide adequate ischemic protection for subjects with one or two of the preexisting conditions. The third mode may be even more extensive than the second mode and may be useful for subjects with multiple preexisting conditions. An appropriate risk score may be calculated based on the number of preexisting conditions, severity of preexisting conditions, their relative weight, as well as a number of patient-specific parameters, such as gender, location ischemia, etc. Such scoring system may be designed as inputs for the controller. In this case, the controller 110 may be configured to calculate or select the most appropriate mode and a respective treatment protocol internally. This information may be communicated to the operator via the display of the controller 110.

DETAILED DESCRIPTION OF THE SECOND PREFERRED EMBODIMENT OF THE INVENTION

In embodiments, the controller 210 may be configured for automatic generation of the input signal and activation of the second treatment protocol. To achieve this, the device may be configured for automatic determination of whether the subject needs the regular or the extended ischemic preconditioning stimulus. This may be achieved by analyzing tissue perfusion changes at the beginning or throughout the delivery of the ischemic preconditioning treatment. According to the present invention, subjects with at least one of the preexisting conditions which are known to attenuate the efficacy of the ischemic preconditioning therapy may be recognized from observing tissue perfusion changes in response to temporary ischemia.

Figure 6:
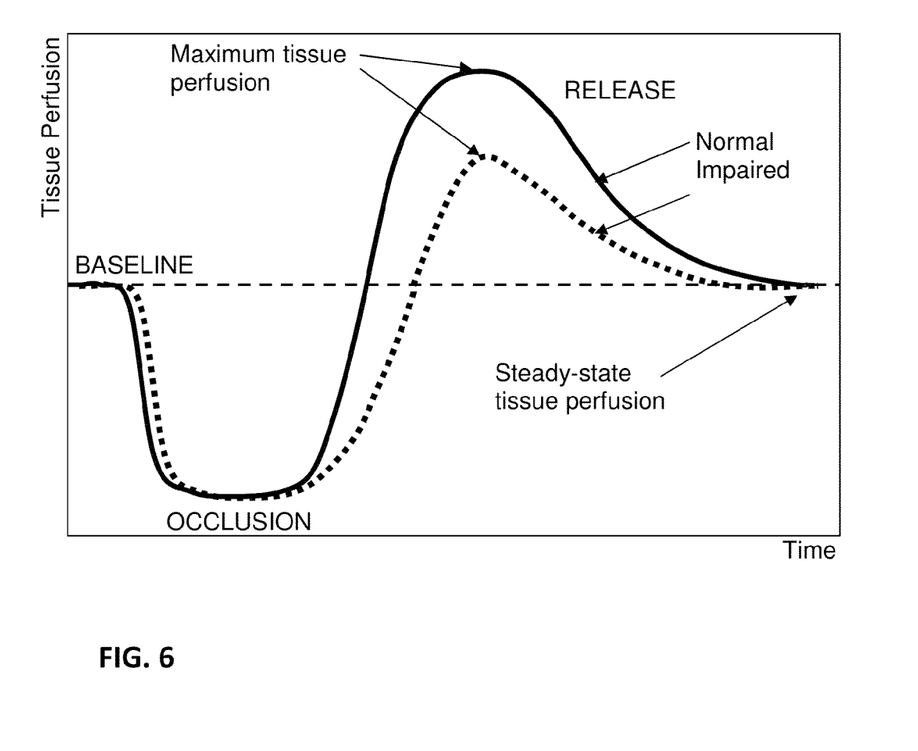
FIG. 6 is a chart indicating normal and impaired tissue perfusion response to an ischemic stimulus.

Flow-mediated dilatation (FMD) is a natural response of tissue to temporary ischemia. In normal subjects, a short interval of ischemia is followed by temporary vasodilatation and increase in blood flow to compensate for ischemic insult. FIG. 6 shows an example of tissue perfusion dynamics in a normal subject (solid line)—tissue perfusion initially drops from its baseline level during occlusion but then exceeds its original pre-ischemic level reaching a maximum level shortly after occlusion is released. The maximum tissue perfusion may exceed the baseline by a factor of two or more. After some time, the tissue perfusion settles back to its initial steady-state level. The degree by which the maximum tissue perfusion exceeds its steady-state level (in absolute terms or as a relative measure such as percent increase) may be used to make a judgment as to the health status of the subject.

Diabetes, advanced age, and other RIPC-attenuating conditions may have a negative effect of the ability of tissue to temporarily increase tissue perfusion after short periods of ischemia. For subjects having these conditions, their response to occlusion may be impaired (shown in broken line) and their maximum tissue perfusion level will exceed their respective steady-state level by a lesser degree. Measuring the maximum and steady-state tissue perfusion levels may therefore be used for identification of a subject with a preexisting condition necessitating activation of the second treatment protocol.

Figure 7:
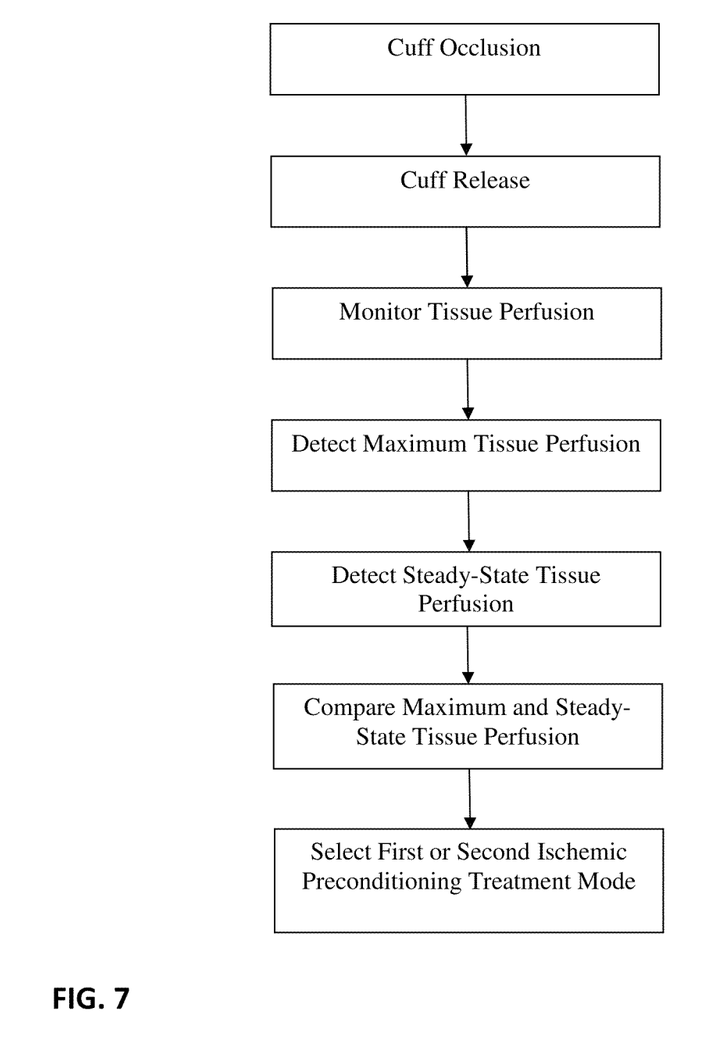
FIG. 7 shows a flow chart of the method of the invention in which selecting of the first or the second mode of preconditioning is done based on detecting maximum and steady-state tissue perfusion parameters during at least one cycle of the preconditioning treatment.

The process of delivery of remote ischemic preconditioning includes a number of short occlusion and release intervals and as such yields itself to a convenient tissue perfusion diagnostic modality which can be done during the procedure itself. In embodiments, a method for automatic selection of the most appropriate mode of ischemic preconditioning treatment includes the following steps—see FIG. 7:
  a. initiating delivery of ischemic preconditioning stimulus by inflating and deflating the cuff positioned about the limb of the subject,
  b. detecting maximum tissue perfusion and steady-state tissue perfusion in the limb,
  c. comparing maximum tissue perfusion with steady-state tissue perfusion, and
  d. selecting to deliver a first treatment protocol if the maximum tissue perfusion exceeds the steady-state tissue perfusion by more than a predetermined threshold, or selecting to deliver the second treatment protocol if the maximum tissue perfusion exceeds the steady-state tissue perfusion by even or less than the predetermined threshold.

The predetermined threshold by which the maximum tissue perfusion should exceed the steady-state tissue perfusion to justify first as opposed to second treatment protocol may be expressed as a percentage of the steady-state tissue perfusion or as an absolute value.

In addition to selecting either a first or second treatment protocol as a result of the treatment, the controller 210 of the device 200 may be configured to select a progressively more extensive treatment protocol in a range between a predetermined first and second treatment protocol depending on the degree by which the maximum tissue perfusion exceeds the steady-state tissue perfusion. The closer is that measure to the predetermined threshold, the more extensive and longer treatment protocol may be selected.

In embodiments, the measurement of the steady state tissue perfusion may be conducted once or multiple times throughout the treatment. Such measurements may be taken at the beginning of the treatment or during one or more release intervals. Maximum tissue perfusion may be taken during release intervals following the first or subsequent occlusion intervals. More than one measurement allows for a more accurate determination of these parameters and minimizes the errors and artifacts that may be associated with a single measurement.

In other embodiments, only maximum tissue perfusion and not steady-state tissue perfusion may be assessed during the remote ischemic preconditioning treatment. It may then be compared against a predetermined maximum tissue perfusion threshold, which may be derived in advance using a database of patients with a known disease state. A second mode may be activated if the maximum measured tissue perfusion is below the predetermined threshold.

In yet other embodiments of the invention, a rate of increase in tissue perfusion (optionally in combination with the maximum and steady-state tissue perfusion levels) may be used to assess the health status of the subject. In healthier subjects, such rate of increase may be higher than in subjects with a preexisting condition described above. Using the rate of increase may be advantageous with short release intervals when the tissue perfusion may not reach its maximum in time for the beginning of the next occlusion interval. This method assumes that a predetermined rate threshold is known in advance so that a comparison against that threshold may be made during the therapy for the purpose of selecting the first or the second mode of operation. Such threshold may be derived from a database of patients with known disease status.

In yet further embodiments, health status of the subject may be assessed by measuring tissue perfusion via excess flow, defined as an area under the curve exceeding the baseline level—see FIG. 6. Healthier subjects will have this area greater than subjects with impaired circulation. Once measured, the excess flow may be compared against a respective excess flow threshold defined in advance using a database of patients with a known disease state. The advantage of this method is that it may be performed using a predetermined fixed duration interval and as such will always fit within the time limit defined by the duration of the release interval.

Yet in other embodiments, once the tissue perfusion measurement is conducted, the controller may be configured to prompt the selection of the most appropriate treatment protocol rather than automatically switching to its execution. Such prompting will leave the final word as to which treatment protocol is used to the operator in charge of treating the subject. If no selection is made within a predetermined period of time, the controller 210 may be configured to execute the treatment protocol automatically according to the above described programs.

Local tissue perfusion may be assessed using a number of known techniques, such as by measuring tissue temperature, level of oxygenation, arterial capillary blood flow, pulse flow, post-capillary venous filling pressure, etc. In embodiments, heat dissipation principle may be used to construct an inexpensive device suitable for accurate assessment of tissue perfusion during remote ischemic preconditioning.

Figure 8:
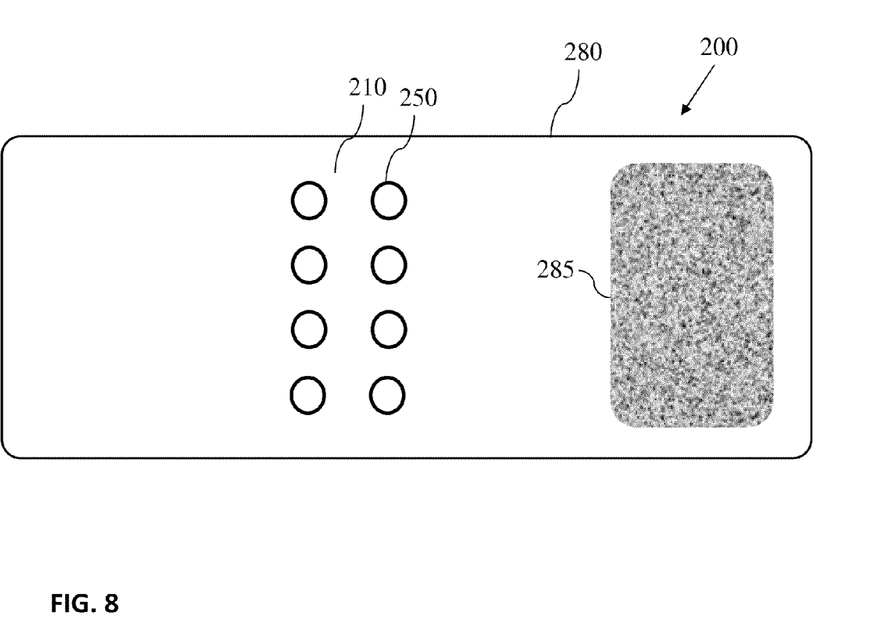
FIG. 8 shows the view from below of the device of the invention equipped with a plurality of tissue perfusion sensors.

FIG. 8 shows an example of one embodiment of the device 200 equipped with tissue perfusion sensors utilizing a heat dissipation principle. One or more tissue perfusion sensors 250 may be embedded at the internal surface of the cuff 280 facing the subject—eight are shown as an example in FIG. 8. The tissue perfusion sensors 250 may include heat plates equipped with an electrically-powered heating element. Temperature of each heat plate may be maintained at a safe constant level somewhat higher than normal skin temperature of the subject, for example at about 30 or about 45 degrees C. Electrical energy may be continuously supplied to each heat plate during the measurement. Normal tissue perfusion causes faster heat dissipation from the surface of the heat plate as compared with impaired tissue perfusion. Recording of the amount of electrical energy needed to maintain the temperature of each heat plate at a preselected constant level may be used to indirectly assess tissue perfusion—both maximum and steady-state levels.

Using more than one tissue perfusion sensors allows increasing the accuracy of the measurements by using commonly known signal processing techniques, for example by taking an average of several measurements or by discarding the max and min values as outliers. Another advantage of having more than one heat plates is the ability to assign different target temperatures for several of the heat plates.

Locating the tissue perfusion sensors at the internal surface of the cuff facing the subject allows them to be naturally pressed against the tissue during the treatment, especially so during the occlusion intervals when the cuff is inflated. Most tissue perfusion measurements, however, may be done during release intervals, calling for additional provisions to assure good contact between the tissue perfusion sensors and the tissue of the limb.

One such provision may be to keep the cuff inflated at a low pressure of about 5-30 mmHg during release intervals. Such low cuff pressure may not interfere with reperfusion but may be helpful to assure a tight fit of the cuff about the limb.

Alternately, the area of the cuff containing the sensors 250 may be equipped with an adhesive layer made from an appropriate heat-conductive material. A protective layer may be also provided and configured to be removed prior to use (by pulling a tab for example) so as to expose the adhesive layer when the cuff is first placed about the limb of the subject.

In yet further embodiments of the invention, measuring blood pressure during the delivery of the ischemic preconditioning treatment may be used to automatically detect hypertension, which may then be used to activate the second mode of treatment. For example, if elevated blood pressure is detected during one or more treatment cycles, the controller may be configured to switch to the second mode. Known predetermined thresholds of elevated blood pressure may be programmed into the processing unit of the controller, for example systolic blood pressure exceeding 160 mmHg or higher. Other measures may also be used such as if a diastolic blood pressure exceeds 100 mmHg or higher on a sustained basis during treatment. Sustained elevation may be defined as detecting blood pressure exceeding a predetermined threshold at least once during at least two cycles of treatment.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for delivery of a remote ischemic preconditioning therapy comprising the steps of:
    a. inflating and deflating a cuff positioned about a limb of a subject according to a predefined first treatment protocol, said first treatment protocol including a first predetermined number of treatment cycles, each of said treatment cycles comprising inflating said cuff to a cuff pressure at or above a limb occlusion pressure of the subject; maintaining said cuff pressure at or above said limb occlusion pressure for a first occlusion interval of at least about one minute; deflating said cuff to a deflated state; and maintaining said cuff in said deflated state for a first release interval,
    b. at any time before initiation of said first treatment protocol as well as during or shortly after the completion of said first treatment protocol identifying said subject as having a preexisting condition necessitating applying a predefined second treatment protocol to provide an ischemic preconditioning stimulus of increased intensity, and
    c. switching delivery of said remote ischemic preconditioning therapy to said second treatment protocol for said subject with said preexisting condition resulting in a total number of treatment cycles or a total treatment time exceeding that of said first treatment protocol.

2. The method as in claim 1, wherein said preexisting condition is selected from a group consisting of diabetes, advanced age, obesity, advanced atherosclerosis, dyslipidemia, hypertension, cardiac hypertrophy, heart failure, history of smoking, history of alcohol or substance abuse, and pharmacological interactions.

3. The method as in claim 2, wherein said pharmacological interactions include using by said subject of a compound selected from a group consisting of statins, beta-blockers, non-steroidal anti-inflammatory drugs, $Ca^{2+}$ channel blockers, recent or excessive caffeine intake, hypoglycemic sulfonylureas, and insulin.

* * * * *